US00PP10902P

United States Patent [19]

Bradford et al.

[11] Patent Number: Plant 10,902

[45] Date of Patent: May 18, 1999

[54] NECTARINE TREE NAMED 'REGAL RED'

[76] Inventors: Lowell Glen Bradford, 12439 E. Savana Rd.; Norman G. Bradford, 11875 E. Savana Rd., both of Le Grand, Calif. 95333

[21] Appl. No.: 08/995,418

[22] Filed: Dec. 19, 1997

[51] Int. Cl.[6] ..... A01H 5/00

[52] U.S. Cl. ..... Plt./190

[58] Field of Search ..... Plt./40.1, 41.1, Plt./190, 187

[56] References Cited

U.S. PATENT DOCUMENTS

P.P. 5,664 2/1986 Bradford et al. ..... Plt./41
P.P. 7,193 3/1990 Bradford et al. ..... Plt./41

*Primary Examiner*—Howard J. Locker
*Assistant Examiner*—Ashwin Mehta

[57] ABSTRACT

The present invention relates to a nectarine tree, *Prunus persica,* and more particularly to a new and distinct variety broadly characterized by a large size, vigorous, self-fertile, productive and regular bearing tree. The fruit matures under the ecological conditions described approximately the first week in August, with first picking on Jul. 28, 1997. The fruit is unifomrmly large in size, acidic in flavor, globose in shape, clingstone in type, very firm and crispy in texture, and nearly full red in skin color. The variety was a first generation cross using 'Red Glen' (U.S. Plant Pat. No. 7,193) nectarine as the selected seed parent and 'September Red' (U.S. Plant Pat. No. 5,664) nectarine as the selected pollen parent.

1 Drawing Sheet

BACKGROUND OF THE VARIETY

In a continuing effort to improve the quality of fresh market and shipping fruits, we, the inventors, typically hybridize a large number of nectarine and peach seedlings each year. The present invention relates to a new and distinct variety of nectarine tree, which has been denominated varietaly as 'Regal Red'. The present variety was developed by us in 1993 in a cultivated area of our experimental orchard at Bradford Farms near Le Grand, Calif. in Merced County (San Joaquin Valley). It was first generation cross using 'Red Glen' (U.S. Plant Pat. No. 7,193) nectarine as the seed parent and 'September Red' (U.S. Plant Pat. No. 5,664) nectarine as the selected pollen parent. Subsequent to origination of the present variety of nectarine tree, we asexually reproduced it by budding and grafting, and such reproduction of plant and fruit characteristics were true to the original plant in all respects. The reproduction of the variety included the use of Nemaguard Rootstock, the standard of the stone fruit industry in central California, upon which the present variety was compatible and true to type.

The present variety is most similar to its seed parent, the 'Red Glen' (U.S. Plant Pat. No. 7,193), by producing clingstone nectarines that are acidic in flavor, very firm in texture, and full red in skin color, but is distinguished therefrom and an improvement thereon by producing fruit that ripens about twelve days later, by having a large blossom instead of small, and by having a bitter kernel instead of sweet. It should be noted that atypical weather conditions occurred in California during 1997, causing stone fruit to mature about 10 days earlier than normal. The first picking of the 'Red Glen' occured on July 15th, while the first picking of the present variety occurred on July 28th.

The present variety is similar to its pollen parent, 'September Red' (U.S. Plant Pat. No. 5,664) by producing clingstone nectarines, but is very distinguished therefrom by producing fruit that ripens about about twenty-five days earlier, that is full red in skin color, and that is firmer.

DRAWINGS

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard eating ripe on Aug. 6, 1997. All major color code designations are by reference to the Inter-Society Color Council, National Bureau of Standards. Common color names are also used occasionally.

Tree

Size: Large, reaching a height of 12' [3.66 meters] after 5 growing seasons utilizing typical dormant pruning.
Vigor: Vigorous, responding positively to irrigation and fertilization.
Growth: Spreading and dense.
Form: Vase formed.
Hardiness: Hardy, able to survive typical winter weather experienced in central California.
Production: Productive, thinning necessary.
Bearing; Regular bearer, with no alternate bearing yet observed.
Fertility: Self-fertile.
Trunk:
- *Size.*—Medium, reaching a diameter of 5" [127 mm.] after five growing seasons.
- *Texture.*—Somewhat shaggy.
- *Bark color.*—Grayish brown [61. gy.Br.].
- *Lenticels.*—Numerous. Color: Strong brown [55. s.Br]. Average Size: ⅛" to ⅜" [3.2–9.5 mm.].

Branches:
- *Size.*—Medium, typical of the species.
- *Texture.*—Smooth on 1st year wood, increasing roughness with age.
- *Color.*—1st Year wood topside: Light grayish red [18. 1.gy.R]. 1st Year wood underside: Brilliant yellow green [116. brill. YG]. Older wood; Moderate brown [58. m.Br].

*Lenticels.*—Numerous, small. Color: Brownish orange [54. brO]. Average Size: 1/16" [1.6 mm].

Leaves:

*Size.*—Medium. Average length: 5¼" [133.4 mm.]. Average width: 1⅝" [41.3 mm.].

*Thickness.*—Medium.

*Form.* —Elliptical.

*Apex.*—Acutely pointed.

*Base.*—Acute.

*Surface.*—Smooth.

*Color.*—Dorsal surface: Moderate olive green [125. m.OlG]. Ventral surface: Moderate yellow green [120. m.YG].

*Margin.* —Finely serrate.

*Venation.*—Pinnately net veined.

*Petiole.*—Average Length: 7/16" [11.1 mm.]. Average Thickness: 1/16" [1.6 mm.]. Color: Brilliant yellow green [116. brill.YG].

*Stipules.*—Numerous, 2 per leaf, up to 6 per growing tip. Average Length: ¼" to ⅜" [6.4–9.5 mm].

*Glands.*—Numbers: 2 to 4 leaf. Position: Alternately positioned on petiole and base of blade. Size: Large. Form: Reniform. Color: Dark grayish red [20. d.gy.R].

Flower buds:

*Hardiness.*—Hardy, with respect to central California winters.

*Diameter.*—Typically ⅜" [9.5 mm.] 1 week before bloom.

*Length.*—Typically ¾" [19.1 mm.] 1 week before bloom.

*Form.*—Free.

*Surface.*—Pubescent.

Flowers:

*Blooming period.*—Medium as compared with other varieties.

*Onset of bloom.*—One percent on Feb. 27, 1997.

*Fragrance.*—Slight to moderate.

*Type.*—Showy.

*Average diameter.*—1¾" [44.45 mm].

*Color.*—Pale purplish pink [252. p.p.Pk].

Fruit

Maturity when described: Hard eating ripe, Aug. 6, 1997. As noted previously, maturity dates were 10 days earlier than normal for 1997.

Date of first picking: Jul. 28, 1997, but typically Aug. 8th.

Date of last picking: Aug. 20, 1997, but typically Aug. 30th.

Size: uniform, large.

*Average diameter axially.*—2¾" [69.9 mm.].

*Average transversely in suture plane.*—2⅝" [66.7 mm.].

*Typical weight.*—6.27 Ounces [178 grams].

Form: Globose, uniform, slightly unsymmetrical.

*Longitudinal section form.*—Round.

*Transverse section through diameter.*—Round.

Suture: An inconspicuous line near the base becoming a shallow groove toward the apex with a slight depression beyond the pistil point.

Ventral surface: Rounded, lipped toward the apex.

Lips: Unequal.

Cavity: Rounded, circular, suture showing on one side, stem marks typical.

*Depth.*—½" [12.7 mm.].

*Breadth.*—⅞" [22.2 mm.].

Base: Rounded to slightly truncate.

Apex: Rounded.

Pistil point: Short, depressed within the suture.

Stem: Medium.

*Average length.*—⅜" [9.5 mm.].

*Average width.*—3/16" [4.8 mm.].

Skin:

*Thickness.*—Medium.

*Texture.*—Medium.

*Tenacity.*—Tenacious to flesh.

*Tendency to crack.*—None observed.

*Color.*—Very dark red [17. v.d.R] mottled into a strong reddish orange [35. S.rO] background with some light yellowish brown [76. l.yBr] freckling.

Flesh:

*Color.*—Brilliant orange yellow [67. brill.OY] with substantial dark red [16. d.R] streaking toward the stone.

*Surface of pit cavity.*—Dark red [16. d.R] fibers breaking when twisted away from the stone.

*Amygdalin.*—Abundant.

*Juice.*—Abundant, rich.

*Texture.*—Very firm, crisp.

*Fibers.*—Abundant, fine.

*Ripens.*—Evenly.

*Flavors.*—Acidic with medium sweetness, strong nectarine flavor, 14 brix average.

*Aroma.*—Slight.

*Eating quality.*—Good.

Stone

Type: Clingstone.

Form: Oval.

Base: Straight.

Apex: Acute.

Hilum: Narrow.

Sides: Equal.

Surface; Horizontally furrowed toward the apex, pitted near the base.

Ridges; Jagged toward the base.

Color: Dark yellowish brown [78. d.yBr].

Pit wall: ¼" [6.4. mm.] thick.

Tendency to split: None observed.

Kernel:

*Form.*—Oval.

*Taste.*—Bitter.

*Viable.*—Yes.

*Average width.*—½" [12.7 mm.].

*Average length.*—¾" [19.1 mm.].

*Skin color.*—Strong yellowish brown [74. s.yBr] with grayish brown [61. gy.Br] veins.

*Pellicle Color.*—Grayish brown [61. gyBr].

*Amygdalin.*—Abundant.

Use

Market: Fresh and long distance shipping.

Keeping quality: Fruit quality observed to remain in good condition in excess of 14 days in cold room at 36° Fahrenheit [2° Celsius].

Resistance to insects: No unusual susceptibilities noted.

Resistance to diseases: No unusual susceptibilities noted.

Although the new variety of nectarine tree possesses the described charcteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to its seed parent, 'Red Glen' (U.S. Plant Pat. No. 7,193), by producing clingstone nectarines that are acidic in flavor, very firm in texture, and full red in skin color, but is distinguished therefrom and an improvement thereon by producing friut that ripens about twelve days late, by having a larg blossom instead of small, and by having a bitter kernel instead of sweet.

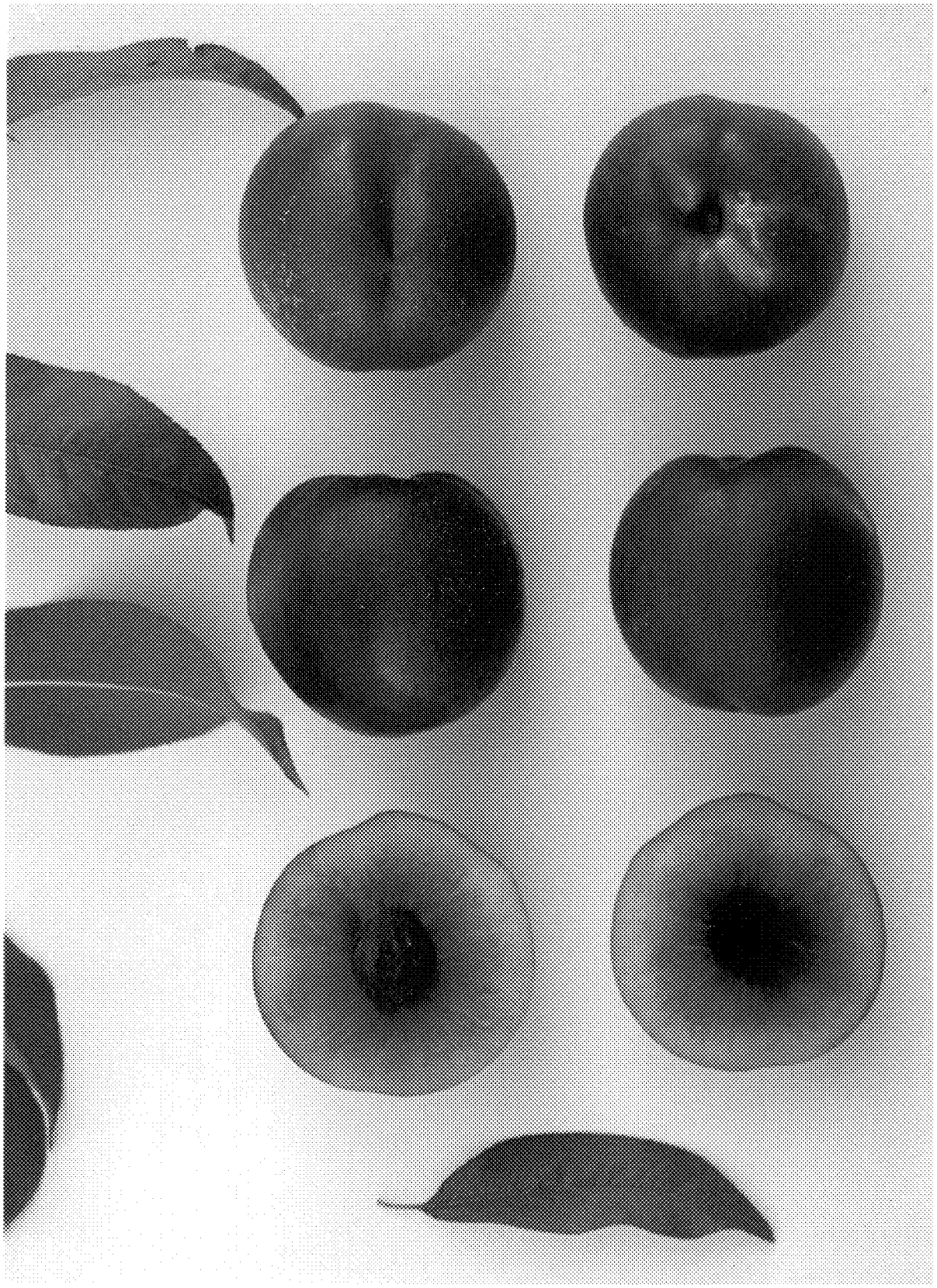

* * * * *